US010052652B2

(12) United States Patent
Pauser et al.

(10) Patent No.: US 10,052,652 B2
(45) Date of Patent: Aug. 21, 2018

(54) CAPSULE FOR MIXING AND DISPENSING A DENTAL MATERIAL

(71) Applicant: 3M INNOVATIVE PROPERTIES COMPANY, St. Paul, MN (US)

(72) Inventors: Helmut Pauser, Diessen (DE); Mathias Bertl, Wildsteig (DE)

(73) Assignee: 3M Innovative Properties Company, St. Paul ( * ) Notice: Subject to any disclaimer, the term of this patent is extended or adjusted under 35 U.S.C. 154(b) by 0 days.

(21) Appl. No.: 15/303,662

(22) PCT Filed: Apr. 6, 2015

(86) PCT No.: PCT/US2015/024468
§ 371 (c)(1),
(2) Date: Oct. 12, 2016

(87) PCT Pub. No.: WO2015/160553
PCT Pub. Date: Oct. 22, 2015

(65) Prior Publication Data
US 2017/0027663 A1 Feb. 2, 2017

(30) Foreign Application Priority Data
Apr. 16, 2014 (EP) .................................. 14164984

(51) Int. Cl.
*A61C 5/06* (2006.01)
*B05C 17/005* (2006.01)
(Continued)

(52) U.S. Cl.
CPC .......... *B05C 17/00566* (2013.01); *A61C 5/62* (2017.02); *A61C 5/64* (2017.02);
(Continued)

(58) Field of Classification Search
CPC ........ B05C 17/00566; B05C 17/00503; A61C 5/68; A61C 5/62; A61C 5/66; A61C 5/64
See application file for complete search history.

(56) References Cited

U.S. PATENT DOCUMENTS 8,893,925 B2    11/2014    Cheetham
8,968,000 B2     3/2015    Leiner
(Continued)

FOREIGN PATENT DOCUMENTS

EP          1741405          1/2007
EP          1759657          3/2007
WO       WO 2001-043799      6/2001

OTHER PUBLICATIONS

International Search Report for PCT International Application No. PCT/US2015/024468, dated May 18, 2015, 3 pages.

*Primary Examiner* — Donnell Long

(57) ABSTRACT

A capsule for mixing and dispensing a dental material which has a body forming a cavity. The cavity is closed by a liquid container. The body and the liquid container in combination form a mixing chamber containing a first component of the dental material. The liquid container has a cup-shaped cartridge formed by a cartridge front wall and a cartridge side wall and having a rear opening. A plug is movably joined within the cartridge through the rear opening for extruding a liquid second component of the dental material. The cartridge further has a channel extending through the cartridge side wall for releasing the second component into the mixing chamber. The body side wall inwardly has a recess being dimensioned for establishing a fluid communication between the channel and the cavity in an activated position, where the activated position corresponds to a second axial position of a two different axial positions of the of the cartridge and the body relative to each other. Further the first axial position corresponds to an inactivated position (Continued)

in which the channel is offset from the recess. A first cover film seals the joint between the cartridge and the plug, and the channel is openably sealed by a second cover film at least in the inactivated position. The capsule helps facilitating the preparation of a dental material.

15 Claims, 2 Drawing Sheets

(51) Int. Cl.
  *A61C 5/64* (2017.01)
  *A61C 5/66* (2017.01)
  *A61C 5/62* (2017.01)
  *A61C 5/68* (2017.01)

(52) U.S. Cl.
  CPC ............... *A61C 5/66* (2017.02); *A61C 5/68* (2017.02); *B05C 17/00503* (2013.01)

(56) References Cited

U.S. PATENT DOCUMENTS

| | | | | |
|---|---|---|---|---|
| 2003/0060749 | A1* | 3/2003 | Aneas | A61M 5/28 604/20 |
| 2007/0048688 | A1* | 3/2007 | Pauser | B05C 17/00593 433/90 |
| 2007/0272567 | A1* | 11/2007 | Peuker | A61C 5/064 206/219 |

* cited by examiner

CAPSULE FOR MIXING AND DISPENSING A DENTAL MATERIAL

FIELD OF THE INVENTION

The invention relates to a capsule for mixing and dispensing a dental material. In particular the invention relates to a capsule for mixing a powder and a liquid which are separately stored and which can be brought together for mixing in a shaker by activating the capsule.

BACKGROUND ART

Dental substances are often provided in devices allowing the substance to be dispensed directly to a desired location, for example on a dental pad or in a patient's mouth. Such dispensing devices typically have a chamber for holding the dental substance, an outlet, and a piston for extruding the substance from the chamber through the outlet.

A variety of dispensing devices are designed for dispensation of relatively high viscosity dental substances, like for example dental filling materials. Some of those dispensing devices are configured for use with an applicator providing an extrusion force that is sufficient for dispensation of high viscosity dental substances. In dentistry several types of manually operated applicators are available which provide leverage for increasing manual forces to provide sufficient extrusion forces. Many applicators are designed as a reusable tool which forms part of a dental practice's basic equipment.

A particular dispensing device often used to store, prepare and dispense a hardenable dental material mixed from a powder and a liquid is the so-called dental capsule in which the mixing of the powder and the liquid is performed within the capsule by shaking the capsule in a shaker.

U.S. Pat. No. 8,893,925 discloses container for mixing and dispensing material. The container comprises a body having a main chamber, a dispensing nozzle, a liquid receptacle and a plunger. The liquid receptacle has a front portion arranged to break away upon pressure being applied by the plunger so that the plunger can traverse the entire length of the body. This enables a charge of material in the main chamber to be entirely dispensed through a frangible wall into the nozzle. The container is particularly envisaged for use in mixing and dispensing of dental materials.

U.S. Pat. No. 8,968,000 discloses a mixing and application capsule for producing and discharging a dental preparation. To prevent a liquid loss, a mixing and application capsule for producing a dental preparation is proposed. The capsule has a body with a mixing chamber for receiving a mixing component and for mixing the dental preparation from the mixing component and a fluid. The capsule further has an outlet opening for discharging the dental preparation. A first plunger body which can be displaced in the body delimits the mixing chamber in the body. The first plunger body has a channel to guide the fluid from a cavity into the mixing chamber and a projection. The capsule has further a second plunger body which can be displaced in the body relative to the first plunger body. The second plunger body has the cavity to receive the fluid. The cavity is configured to receive the projection of the first plunger body.

Such capsules have a variety of advantages as, for example, a relatively long shelf life. However there is a still desire for a capsule with such a long shelf life, which is easy to use and which is nevertheless relatively inexpensive.

SUMMARY OF THE INVENTION

The invention relates to a capsule for mixing and dispensing a dental material. The capsule comprises a body having a front end and a rear end and extending along a longitudinal axis. The body forms a body front wall and a body side wall. The body side wall protrudes from the front wall in a dimension of the longitudinal axis. The body front wall and the body side wall in combination form a cavity which extends into the body from the rear end of the body toward the body front wall. The cavity merges in an outlet through the body front wall. Further the cavity is closed by a liquid container adjacent the rear end of the body. The body and the liquid container in combination form a mixing chamber. In particular the body and the liquid container preferably form a closed space between which can be used as mixing chamber for mixing the dental material. The mixing chamber contains a first component of the dental material.

The liquid container comprises a cup-shaped cartridge formed by a cartridge front wall and a cartridge side wall. The cartridge has a rear opening. The rear opening is preferably formed by a free end of the cartridge side wall opposite of the cartridge front wall. A plug is movably joined or arranged within the cartridge through the rear opening of the cartridge. The plug is adapted for extruding a liquid second component of the dental material. Such second component is contained between the plug and the cartridge, preferably in a space formed between the plug and the cartridge. The liquid is preferably extrudable by a movement of the plug into the cartridge along the longitudinal axis. The cartridge further has a channel which extends through the cartridge side wall. The channel is adapted for releasing the second component into the mixing chamber. The channel extends preferably in a dimension generally laterally to the longitudinal axis.

The body side wall inwardly (at the side of the side wall delimiting or facing the cavity) has a recess being dimensioned for establishing a fluid communication between the channel and the cavity in an activated position. The activated position corresponds to a second axial position of a first and a second axial position of the cartridge and the body relative to each other in a dimension along the longitudinal axis. The first axial position corresponds to an inactivated position in which the channel is offset from the recess. In the inactivated position a portion of the body side wall offset from the recess covers passage.

A first cover film seals the joint between the cartridge and the plug. Further the channel is openably sealed by a second cover film at least in the inactivated position.

The invention is advantageous in that it provides a liquid container for storing a liquid in a tightly sealed configuration. Further the invention provides a capsule which can be activated for use relatively easily. In particular, although the capsule of the invention allows for tightly sealing a liquid, the seal can be opened for activation of the capsule by applying only relatively low forces to the capsule. In contrast to some prior art capsules which require high forces and therefore a separate tool for activation, the present invention provides a capsule that normally can be activated manually. Further the capsule of the invention allows for storing an amount of liquid which can be selected from a relatively wide range of different amounts, from very low amounts to relatively high amounts, without substantially modifying the configuration of the capsule. Further the capsule of the present invention provides a relatively precise mixing ratio of the dental material because the capsule allows for controlling the amount of liquid used for preparing the dental material relatively precisely. Additionally the capsule of the invention is relatively easy to use and relatively inexpensive in manufacturing.

In an embodiment in the inactivated position the second cover film is mechanically supported by the body side wall. In particular the second cover film may be clamped between the cartridge and the body side wall with the recess and the channel being offset from each other. The offset is in a dimension parallel to the longitudinal axis. Thus in the inactivated position there is preferably no space between the second cover film and the body side wall in the area of the channel. Accordingly the second cover film is backed up by the body against any pressure built up in the liquid in the liquid chamber. In the inactivated position the body therefore prevents any substantial deformation of the second cover film in an area of the channel.

In an embodiment the second cover film and the cartridge are sealingly connected in an area surrounding the channel. In particular the channel extends through the cartridge side wall and preferably forms a channel opening at an outer periphery of the cartridge. This channel opening is preferably entirely covered by the second cover film. Further the second cover film preferably overlaps a circumferential area outside the channel opening and is entirely circumferentially sealed in this overlapping area.

In an embodiment the connection between the second cover film and the cartridge forms a pre-determined breaking point. The pre-determined breaking point is adapted to break upon exceeding a force exerted to the connection from hydraulic pressure built up in the second component. The pre-determined breaking point may be formed by a weakened area, for example one or more notches in the cover film.

In an embodiment the first and second cover film are formed by portions of the same cover sheet. The cover sheet may comprise at least one polymeric layer and a metal layer and being formed as a circumferential sleeve. Such a cover sheet may comprise a contiguous layer of metal, preferably an aluminum layer. In one example the aluminum layer has a thickness of between 0.008 mm and 0.1 mm, preferably about 0.03 mm. The metal layer is preferably generally adapted to block substances, in particular air and moisture from permeating through the cover sheet. Preferably the cover sheet further comprises a polymeric layer, preferably a layer comprising or consisting of polyethylene. This allows for the cover sheet to be heat sealed with the polymeric layer to the preferably thermoplastic cartridge and plug. Heat sealing may be performed using a heated tool or by ultrasonic welding, for example. Further the thermoplastic layer forms a protective layer for the metal layer so as to avoid undesired chemical or physical interaction between the liquid and the metal layer. The configuration of the cover sheet can be identically used for the first cover film and/or the second cover film.

In a further embodiment the cover sheet extends, preferably entirely, circumferentially around the liquid container about the longitudinal axis. Further the cover sheet may be circumferentially sealed (preferably entirely circumferentially sealed) with the cartridge as well as with the plug. The cover sheet may be provided in the form of a sleeve. The sleeve may be made in a seamless manner by extrusion or co-extrusion of polymeric materials. Alternatively the sleeve may be obtained by welding or gluing a sheet together along opposing ends, for example one comprising an aluminum layer.

In one embodiment the first and second cover film are formed monolithically with the cartridge. In this embodiment the first and second cover film may be provided by injection molding in one step with injection molding the cartridge. Further in this embodiment a metal layer (for example aluminum) may be provided by vapor deposition of the metal. Thus the polymeric first and second cover film may be provided with a barrier for moisture and/or solvents. The so formed first cover film may extend, preferably entirely, circumferentially about the longitudinal axis and may be, preferably entirely, circumferentially sealed with the plug.

In a further embodiment at least a portion of the first cover film corresponds to a concertina hose. Thus the first cover film may automatically fold in a controlled manner as the plug is moved into the cartridge.

In a preferred embodiment the capsule further has a nozzle for dispensing the dental material. The nozzle is preferably movable between a dispensing position and a storage position. In the dispensing position the nozzle is preferably in fluid communication with the outlet and in the storage position the nozzle preferably closes the outlet. The dispensing position may comprise several geometric positions between the nozzle and the body, or a range between two geometric extreme positions. For example the dispensing position of a nozzle that is pivotable with respect to the body may within the dispensing position be pivotable over an angular range whereas the storage position is outside that angular range.

In an embodiment the capsule comprises a powder within the mixing chamber. The powder and the liquid are adapted to form in combination a hardenable dental material. The powder may be a glass powder or resin modified glass powder. The liquid may be a water based polyacid or a monomer based polyacid with light initiator.

In a further embodiment the body comprises a catch for retaining the capsule in a dispensing gun.

DETAILED DESCRIPTION OF THE INVENTION

Figure 1:
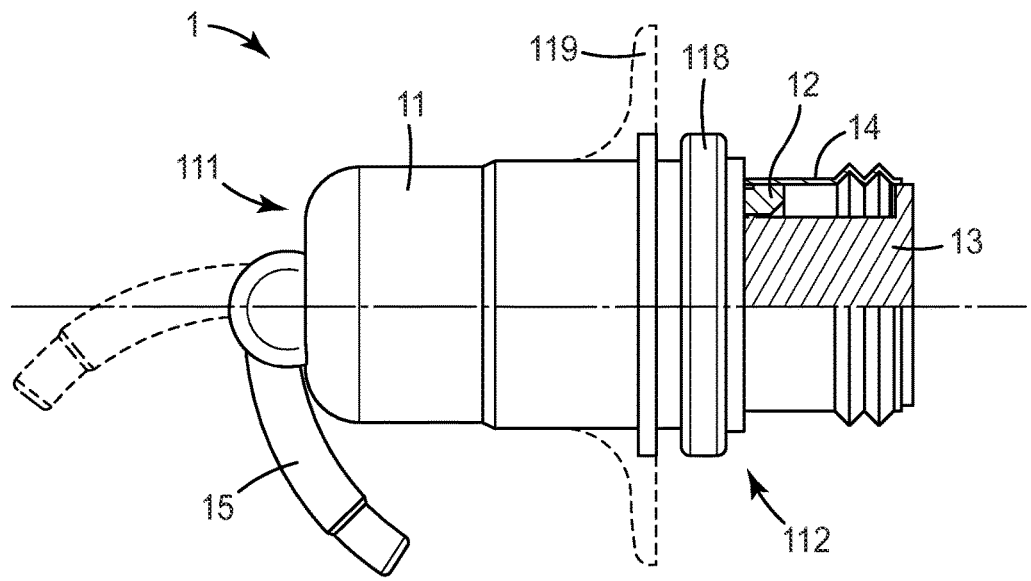
FIG. 1 is an exterior view of a capsule according to an embodiment of the invention.

FIG. 1 shows a capsule 1 for mixing and dispensing a dental material. The capsule 1 has a body 11 with a front end 111 and a rear end 112. The capsule 1 further has a cartridge 12 movably received within the body 11 and a plug 13 movably received within the cartridge 11. The cartridge 12 and the plug 13 in combination form a liquid container which in the example is pre-filled with a liquid component of the dental material (not visible in this view). The body 11 further forms a mixing chamber therein which in the example is partly filled by a powdery further component of the dental material (also not visible in this view). The components can be brought together in the mixing chamber by activation of the capsule 1, in particular by pushing the plug 13 into the cartridge 12. Subsequently the capsule 1 can be placed in a shaker unit (not shown) for mixing the components by shaking the capsule 1 over a certain period of time.

The powder and the liquid are preferably adapted to form a hardenable composition in combination. An exemplary powder material comprises a glass powder or resin modified glass powder. And an exemplary liquid comprises a water based polyacid or a monomer based polyacid with light initiator. The mixture from the powder and the liquid typically forms a pasty material which can be extruded from the capsule 1 by pushing the cartridge 12 into the body 11.

The capsule therefore has a nozzle 15. The nozzle 15 is movable, in the example pivotable, between a storage position (shown) and a dispensing position (indicated by dashed line) in which mixed dental material can be extruded from the capsule 1. In the example the nozzle 15 is pivotably and inseparably connected with a portion of the body 11. This may be achieved by first molding the nozzle 15 and subsequently overmolding the nozzle 15 by the body 11.

Further the capsule 1 has a catch 118 for retaining the capsule 1 in a dispensing gun (not shown). Such a dispensing gun is for example commercially available under the designation 3M™ ESPE™ Capsule Dispenser form the company 3M Deutschland GmbH, Germany. The catch 118 in the example is formed by a circumferential bulge at the rear end 112 of the body 11. A circumferential rim 119 is arranged spaced from the catch 118 further to the front end 111 of the body. As indicated by the dashed line the rim 119 may form a finger plate. The finger plate can assist in retaining the capsule manually while activating the capsule 1 for bringing the powder and the liquid in contact with each other.

Figure 2:
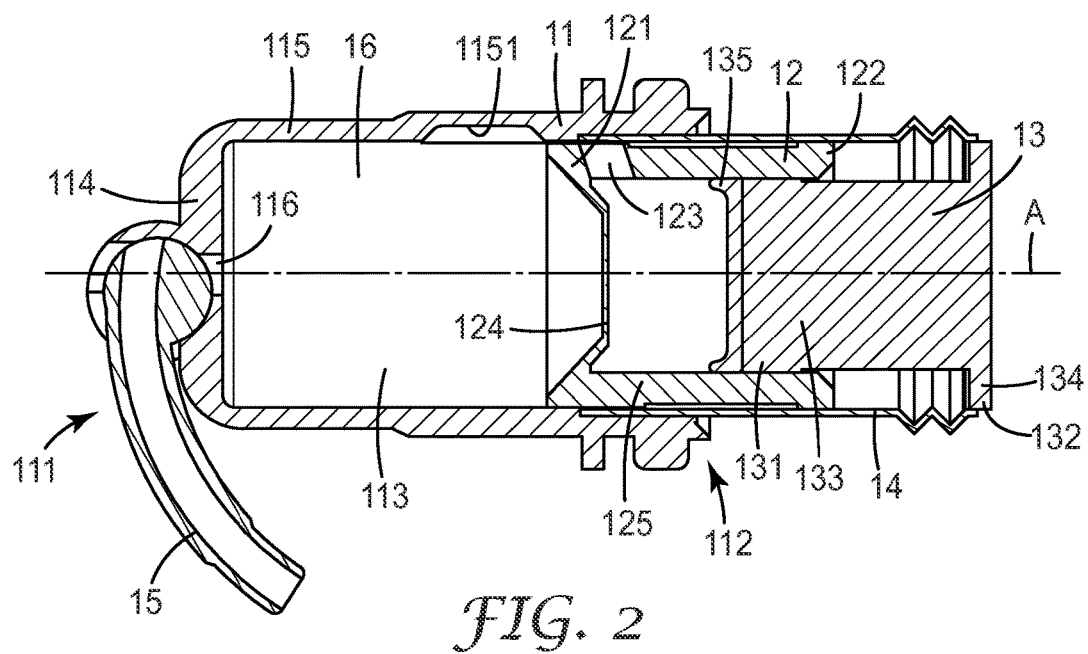
FIG. 2 is a cross-sectional view of a capsule according to an embodiment of the invention.

FIG. 2 shows the capsule 1 in a cross-sectional view more detail. The capsule generally extends along a longitudinal axis A. The body 11 of the capsule 1 forms a body front wall 114 from which a body side wall 115 protrudes toward the rear end 112 of the body 11. The body side wall at least inwardly extends at a uniform cross-section, for example circular or elliptical, along the longitudinal axis A. The body front wall 114 and the body side wall 115 in combination form a cavity 113 which extends from the rear end 112 into the body 11. The cavity 113 merges adjacent the front end 111 of the body 11 in an outlet 116 through the body front wall 114. The cavity 113 is closed by the cartridge 12 so that a closed mixing chamber 16 is formed within the capsule 1 between the body 11 and the cartridge 12. At the initial stage shown the capsule 1 is not yet activated, and cartridge 12 is positioned spaced from the body front wall 114. At the initial stage further the mixing chamber is preferably (partially) filled with a powder material and the liquid container (formed by the cartridge and the plug 13) is preferably filled with a liquid.

The capsule 1 is adapted to be activated by a user. Such an activation of the capsule 1 causes the liquid to be transferred into the mixing chamber, as further described in detail in the following. Once the capsule 1 is activated it can be placed in a shaker for mixing the powder and the liquid. During mixing the nozzle 15 is normally positioned in the storage position in which the nozzle 15 closes the outlet 116. Thus no dental material can escape from the capsule 1 during mixing. After mixing the nozzle 15 can be turned toward the dispensing position. In the dispensing position the nozzle 15 opens the outlet 116 of the capsule 1 for dispensing the dental material through the nozzle 15.

The cartridge 12 has a cartridge front end 121 and a cartridge rear end 122. Further the cartridge is cup-shaped and has a cartridge front wall 124 and a cartridge side wall 125. The cartridge side wall 125 extends at a generally uniform cross-section, for example circular or elliptical. The cartridge 12 is arranged within the cavity 113 of the body 11 such that the cartridge side wall 125 extends in a dimension of the longitudinal axis A. A channel 123 extends through the cartridge side wall 125. The channel 123 extends generally laterally to the longitudinal axis A. In the example the plug 13 is generally mushroom-shaped with a stem portion 133 arranged at a front end 131 and a widened head portion 134 arranged at a rear end 132 of the plug 13. The stem portion 133 extends at a generally uniform cross-section, for example circular or elliptical. The stem portion 133 further forms a seal structure 135 adjacent the plug front end 131 for sealing with the cartridge side wall 125 of the cartridge 12. The plug 13 is arranged within the cartridge 12 such that stem portion 134 extends in a dimension of the longitudinal axis A.

The capsule 1 further has a cover sheet 14 which is arranged entirely circumferentially around the cartridge side wall 125 and the plug 13. The cover sheet 14 thus forms a sleeve extending at a generally uniform cross-section and along the longitudinal axis A. In particular the cover sheet 14 is entirely circumferentially sealed with the head portion 134 of the plug 13 and entirely circumferentially sealed with the cartridge side wall 125. Thus the cover sheet 14 hermetically seals the joint between the cartridge 12 and the plug 13. Further the cover sheet 14 extends over the channel 123 and is preferably sealed at the cartridge side wall 125 around the channel 123. Thus the cover sheet 14 also hermetically seals the channel 123. Accordingly the liquid container is overall hermetically sealed by the cover 14. The skilled person will recognize that two cover sheets or cover films may be used instead of one single cover sheet as shown in the example.

The cover sheet 14 forms a pre-determined breaking point either within the cover sheet 14 and/or in the sealed connection with the cartridge 12. For example the cover sheet 14 may be formed of at least one polymeric layer and a metal layer (for example aluminum layer), and only the polymeric layer may comprise weakened line. The cover sheet 14 in this example is arranged with the weakened line over the channel 123. Because the metal layer is contiguous the cover sheet 14 still hermetically seals the channel 123, but is enabled to rupture at the weakened line from hydraulic pressure exerted to the cover sheet 14 in the area over the channel 123. In addition or alternatively the cover sheet 14 and the cartridge may be separably sealed with each other such that the cover sheet 14 separates from the cartridge 12 upon exceeding a certain separation force. Such a separable seal can be provided by heat sealing at pre-determined limited sealing parameters (temperature, time and pressure) or by a pressure sensitive adhesive, for example.

Figure 3:
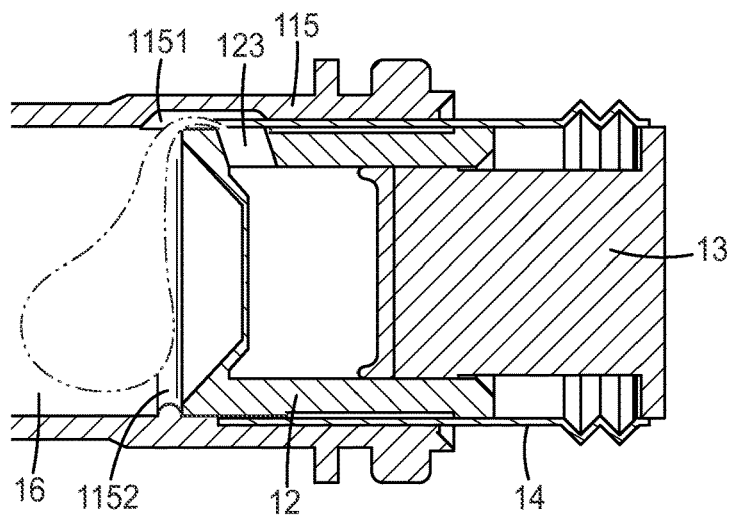
FIG. 3 is a partial cross-sectional view of a capsule according to an embodiment of the invention.

For activation of the capsule 1 the plug 13 is urged toward the body 11. The plug 13 thus exerts a pressure to the liquid contained between the cartridge 12 and the plug 13. At the initial position the channel 123 of the cartridge 12 is offset from a recess 1151 which is arranged in the body side wall 115. Accordingly a portion of the body side wall 115 outside the recess mechanically supports the cover sheet 14. Thus the pressure generated in the liquid causes a pressure to be exerted on the portion of the cover sheet 14 extending over the channel 123, however due to the support by the body side wall 115 cannot deform or rupture. Therefore in the initial position the liquid cannot escape from the liquid chamber so that urging the plug 13 causes the cartridge 12 to move into the body 11 due to hydraulic force transmission from the plug 13 to the cartridge via the liquid. Once the cartridge 12 has moved in a position in which the channel 123 overlaps with the recess 1151 as shown in FIG. 3 the cover sheet 14 is no longer supported by the body side wall 115. Accordingly pressure generated in the liquid pressurized the portion of the cover sheet 14 extending over the channel 123 and upon exceeding a certain pressure causes the cover sheet 14 to rupture. In consequence a fluid communication is established between the channel 123 and the mixing chamber 16 (in the cavity 113) and the liquid can be transferred into the mixing chamber 16. In practice a user may push the plug 13 against the body 11, for example by holding the body 11 and pushing the capsule 1 with the plug 13 oriented downwards on a tabletop. Once the user applies a certain pushing force, the cover sheet 14 ruptures followed by the liquid immediately flowing over into the mixing chamber 16. Typically a user cannot react fast enough to release the pushing force before all of the transferrable liquid is transferred. Thus the capsule 1 provides for a relatively reliable mixing ratio of the powder and the liquid after activation.

For stopping the cartridge 12 at the position in which the channel 123 and the recess 1151 overlap the body side wall 115 inwardly comprises a stop 1152, in the example an annular bulge. The stop 1152 provides for retaining the cartridge 12 during activation to prevent the cartridge moving further into the mixing chamber. However the stop 1152 is adapted such that its retention capacity can be overcome applying a sufficient force. Such a sufficient force can be provided by a dispensing gun which typically converts a hand force into a 5 to 10 times or even higher extrusion force. Therefore during manual activation of the capsule the cartridge can be reliably stopped by the stop 1152, whereas for extruding the mixed dental material using a dispensing gun the cartridge can be moved over the stop 1152.

Figure 4:
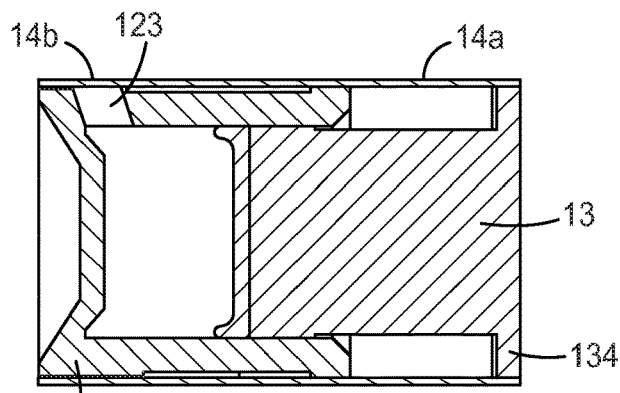
FIG. 4 is a cross-sectional view of a liquid container of a capsule according to an embodiment of the invention.

FIG. 4 shows a further embodiment of a cartridge 12. The cartridge 12 has a first cover film 14a and a second cover film 14b which are monolithically formed with the cartridge 12. The first cover film 14a extends toward a free end circumferentially and at a generally uniform ring-shaped cross-section. The first cover film 14a is sealed at its free end entirely circumferentially to the head portion 134 of the plug 13. Further the second cover film 14b is arranged within the channel 123. The second cover film 14b may form a weakened connection with the remainder of the cartridge 12, for example a thinned or notched portion partially or entirely extending adjacent boundaries of the channel 123. Such first and second cover film 14a, 14b may be formed in a single injection molding step together with molding the cartridge 12.

Figure 5:
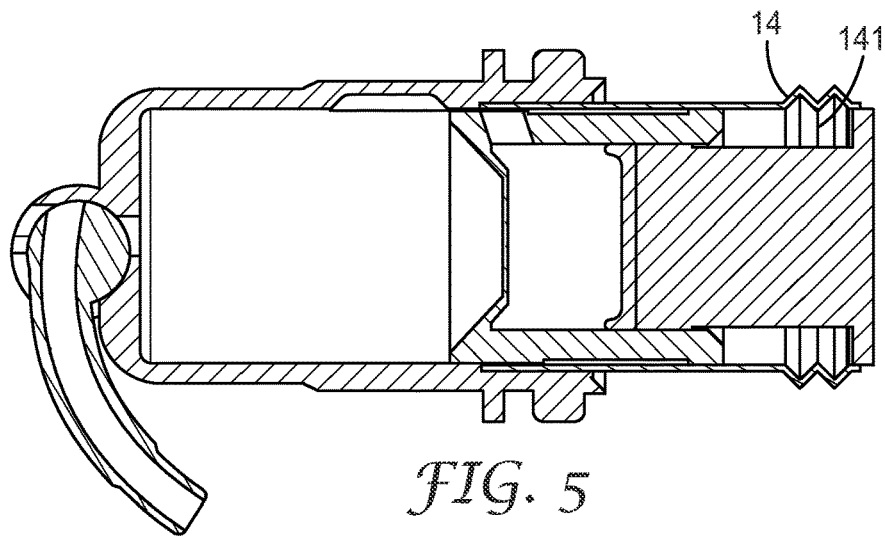
FIG. 5 is a cross-sectional view of a capsule according to a further embodiment of the invention.

FIG. 5 shows a capsule 1 in which the cover sheet 14 has a concertina hose structure 141. Such a concertina hose structure 141 provides for controlled folding or gathering of the cover sheet 14 upon the plug 13 and the cartridge 12 being moved toward one another.

Generally the body 11, the cartridge 12, the plug 13 and the nozzle 15 may be made of a polymeric material and are preferably manufactured by injection molding. Preferred polymeric materials comprise polypropylene, polyethylene, polycarbonate, polyoxymethylene and polyamide. The skilled person will however recognize other polymeric materials depending on the requirements of individual parts to be manufactured from those. The cover sheet 14 or the first and second cover film 14a, 14b may be made of at least a polyethylene or polypropylene layer in combination with a metal layer (preferably an aluminum layer).

The invention claimed is:

1. A capsule for mixing and dispensing a dental material, comprising:
a body having a front end and a rear end and extending along a longitudinal axis;
the body forming a body front wall and a body side wall which protrudes from the front wall in a dimension of the longitudinal axis;
the body front wall and the body side wall in combination form a cavity extending into the body from the rear end toward the body front wall;
the cavity merging in an outlet through the body front wall and being closed by a liquid container adjacent the rear end;
the body and the liquid container in combination forming a mixing chamber containing a first component of the dental material;
wherein the liquid container comprises:
a cup-shaped cartridge formed by a cartridge front wall and a cartridge side wall and having a rear opening;
a plug being movably joined within the cartridge through the rear opening for extruding a liquid second component of the dental material;
the cartridge further having a channel extending through the cartridge side wall for releasing the second component into the mixing chamber;
wherein the body side wall inwardly has a recess being dimensioned for establishing a fluid communication between the channel and the mixing chamber in an activated position;
wherein the activated position corresponds to a second axial position of a first and a second axial position of the of the cartridge and the body relative to each other in a dimension along the longitudinal axis;
wherein the first axial position corresponds to an inactivated position in which the channel is offset from the recess;
wherein a first cover film seals the joint between the cartridge and the plug; and
wherein the channel is openably sealed by a second cover film in the inactivated position, and wherein the channel is at least initially openably sealed by the second cover film in the activated position.

2. The capsule of claim 1, wherein in the inactivated position the second cover film is mechanically supported by the body side wall.

3. The capsule of claim 1, wherein the second cover film and the cartridge are sealingly connected in an area surrounding the channel.

4. The capsule of claim 3, wherein the connection forms a pre-determined breaking point.

5. The capsule of claim 1, wherein the first and second cover film are formed by portions of a single cover sheet.

6. The capsule of claim 5, wherein the cover sheet extends circumferentially around the liquid container about the longitudinal axis and being circumferentially sealed with the cartridge as well as with the plug.

7. The capsule of claim 5, wherein the cover sheet comprises at least one polymeric layer and a metal layer and being formed as a circumferential sleeve.

8. The capsule of claim 1, wherein the first and second cover film are formed monolithically with the cartridge.

9. The capsule of claim 8, wherein the first cover film extends circumferentially about the longitudinal axis and is circumferentially sealed with the plug.

10. The capsule of claim 1, wherein at least a portion of the first cover film corresponds to a concertina hose.

11. The capsule of claim 1, further having a nozzle for dispensing the dental material.

12. The capsule of claim 11, wherein the nozzle is movable between a dispensing position and a storage position, wherein in the dispensing position the nozzle is in fluid communication with the outlet and in the storage position the nozzle closes the outlet.

13. The capsule of claim 1, comprising a powder within the mixing chamber, wherein the powder and the liquid are adapted to form in combination a hardenable dental material.

14. The capsule of claim 1, wherein the body comprises a catch for retaining the capsule in a dispensing gun.

15. The capsule of claim 1, wherein the second cover film forms a pre-determined breaking point.

* * * * *

UNITED STATES PATENT AND TRADEMARK OFFICE
CERTIFICATE OF CORRECTION

| | | |
|---|---|---|
| PATENT NO. | : 10,052,652 B2 | Page 1 of 1 |
| APPLICATION NO. | : 15/303662 | |
| DATED | : August 21, 2018 | |
| INVENTOR(S) | : Helmut Pauser | |

It is certified that error appears in the above-identified patent and that said Letters Patent is hereby corrected as shown below:

On the Title Page

Column 1, Assignee
Line 2, Delete "Paul" and insert -- Paul, MN (US) --, therefor.

Column 2, Abstract
After "positions" delete "of the".

In the Claims

Column 8
Line 29, In Claim 1, before "cartridge" delete "of the".

Signed and Sealed this
Sixteenth Day of April, 2019

Andrei Iancu
*Director of the United States Patent and Trademark Office*